United States Patent [19]

Meilland, deceased

[11] Patent Number: Plant 7,117

[45] Date of Patent: Jan. 23, 1990

[54] ROSE PLANT—MEIGEROKA VARIETY

[75] Inventor: Marie-Louise Meilland, deceased, late of Antibes, France, by Jean-Pierre Le Naour, legal representative

[73] Assignee: The Conard-Pyle Company, West Grove, Pa.

[21] Appl. No.: 136,382

[22] Filed: Dec. 22, 1987

[51] Int. Cl.[4] ..... A01H 5/00

[52] U.S. Cl. ..... Plt./1

[58] Field of Search ..... Plt./1

*Primary Examiner*—Robert E. Bagwill

*Attorney, Agent, or Firm*—Burns, Doane, Swecker & Mathis

[57] ABSTRACT

A new and distinct variety of shrub rose plant is provided which forms attractive semi-double dark carmine pink blossoms. The blossoms are formed abundantly and continuously and possess firm petals which detach cleanly. The vegetation is vigorous. The new variety is not particularly affected by crytogamic diseases, and is well suited for use as ornamentation in parks and gardens.

1 Drawing Sheet

SUMMARY OF THE INVENTION

The new variety of shrub rose plant of the present invention is a sport of the Meigekanu variety (U.S. Plant patent application Ser. No. 895,451, filed Aug. 11, 1986). The Meigekanu variety sometimes has been called the La Sevillana variety.

The new variety forms blossoms which are of the same general shape as the Meigekanu variety, but are distinguished therefrom by a dark carmine pink coloration rather than the red coloration of the Meigekanu variety which is luminous vermilion red on the upper surface and turkish red on the under surface.

The sport of the present invention was the result of the selective study of plants resulting from the budding of eyes of the Meigekanu variety. This selective study resulted in the identification of a single plant of the new variety. The causation of the mutation is unknown.

It is found that the new variety of shrub rose plant possesses the following combination of characteristics:

(a) forms throughout the season attractive semi-double blossoms which are dark carmine pink in coloration;
(b) forms petals which are firm and drop off cleanly,
(c) exhibits a bushy growth habit,
(d) exhibits good disease resistance, and
(e) is particularly well suited for growing in the landscape.

The new variety meets the needs of the horticultural industry for all uses. It can be grown to advantage as an attractive ornamentation in parks, gardens, public areas, and residential landscapes.

The characteristics of the new variety have been found to be homogeneous and stable and are strictly transmissible by asexual propagation from one generation to another.

The new variety has been named the Meigeroka variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety illustrated in the photograph were one year old plants grown during June, 1989 in the open air at West Grove, Pa. on their own roots.

The photograph shows representative blossoms in various stages of opening at the top, representative buds before and after the sepals open at the center right, representative leaves with five leaflets on the left showing the upper (top) and under (bottom) surfaces, a representative leaf with three leaflets on the right showing the upper surface, and a section of a main branch in the center.

DETAILED DESCRIPTION

The chart used in the identification of the colors is that of The Royal Horticultural Society (R.H.S. Colour Chart). The terminology preceding the numbered references has been added to designate in common terms the corresponding colors. The description is based on two year old specimens of the new variety while grown outdoors at Cannet-des-Maures, Var, France when grafted on *Rosa frobelii* understock.

Class: Shrub.

Plant:

*Height.*—Approximately 80 to 85 cm. on average.

*Habit.*—Bushy, spreading.

Branches:

*Color.*—Young stems: light green, Yellow-Green Group 144B, more or less shaded with reddish brown. Adult wood: light green, Yellow-Green Group 144A.

Leaves:

*Stipules.*—Adnate, pectinate, wide and linear.

*Petioles.*—Upper surface: grooved, reddish on young foliage and medium green on adult foliage with more or less glandular edges. Under surface: light green.

*Leaflets.*—Number: 3, 5 and 7 (most often). Shape: oval, rounded at the base, wide and pointed at the apex. Serration: simple and regular. Texture: leathery. General appearance: average ample and dense foliage, with a semi-glossy aspect. Color (young foliage): upper surface: dark green, a bit lighter than Yellow-Green Group 147A. under surface: light green, Yellow-Green Group 147C. Color (adult foliage): upper surface:

bronzed green, a bit darker than Yellow-Green Group 146B. Under surface: light green, Yellow-Green Group 146D.

Inflorescence:

*Number of flowers.*—Approximately 5 to 20 per stem.

*Peduncle.*—Straight, rigid, more or less shaded with a reddish-brown coloration, approximately 5 cm. in length on average.

*Sepals.*—Upper surface: tormentose, greenish in coloration, more or less shaded with reddish brown. Under surface: light green, more or less shaded with red, more or less glandular, the outside petals are slightly appendiculated.

*Buds.*—Shape: conical. Length: approximately 2.1 cm. on average. Size: small. Color: upper surface: dark carmine pink, Red Group 52A, lighter on the outside petals. Under surface: carmine pink, Red Group 52B.

*Flower.*—Form: semi-double, opens initially as a hollow cup, and subsequently assumes a flattened configuration. Diameter: approximately 8 cm. on average. Color (when opening begins): upper surface: dark carmine pink, Red Group 52A, slightly lighter on the outside petals. Under surface: carmine pink, Red Group 52B. Color (when blooming): upper surface: medium carmine pink, Red Group 52A. Under surface: carmine pink, Red Group 52B. Color (at end of opening): upper surface: pale carmine pink, Red Group 52D, becoming white towards the base of the petals. Under surface: light carmine pink, Red Group 52C. Fragrance: none. Lasting quality: long. Petal form: widely rounded tip with a small point at the apex, wide base, some of the inside and outside petals commonly exhibit a longitudinal white stripe, and a white area commonly is present on both sides of the petals at the base. Texture: firm. Petal number: approximately 10 to 15 on average. Petal drop: good. Stamen number: approximately 45 on average. Anthers: normal and yellow in coloration. Filaments: yellow base, light fuchsine top. Pistils: approximately 45 on average. Stigmas: normal, yellowish in coloration. Styles: free, twisted, greenish yellow in coloration, irregular in height. Receptacle: light green, more or less shaded with red at the dehiscence of the anthers and in longitudinal section is narrow and jug shaped.

Development:

*Vegetation.*—Very vigorous.

*Blooming.*—Abundant and continuous.

*Aptitude to bear fruits.*—Good.

*Resistance to frost.*—Good.

*Resistance to diseases.*—Above average.

I claim:

1. A new and distinct variety of shrub rose plant characterized by the following combination of characteristics:

(a) forms throughout the season attractive semi-double blossoms which are dark carmine pink in coloration, (b) forms petals which are firm and drop off cleanly, (c) exhibits a bush growth habit, (d) exhibits good disease resistance, and (e) is particularly well-suited for growing in the landscape;

substantially as herein shown and described.

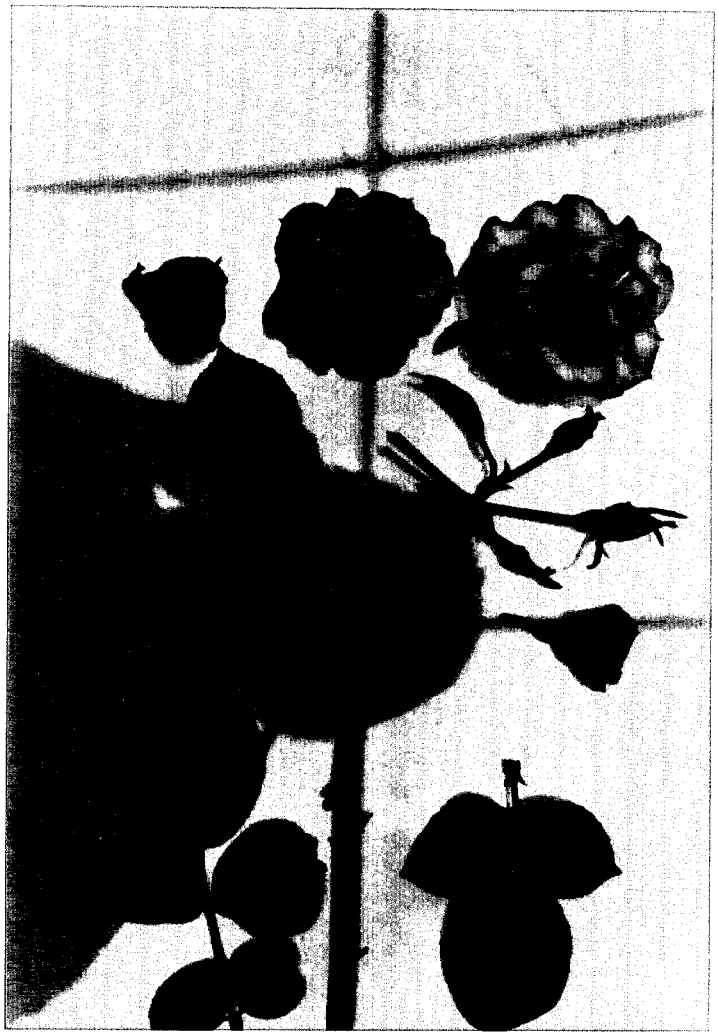

* * * * *